(12) United States Patent
Tsoneva et al.

(10) Patent No.: US 11,202,882 B2
(45) Date of Patent: Dec. 21, 2021

(54) SYSTEM AND METHOD FOR FACILITATING WAKEFULNESS

(71) Applicant: KONINKLIJKE PHILIPS N.V., Eindhoven (NL)

(72) Inventors: Tsvetomira Kirova Tsoneva, Eindhoven (NL); Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 173 days.

(21) Appl. No.: 16/466,074

(22) PCT Filed: Dec. 5, 2017

(86) PCT No.: PCT/EP2017/081536
§ 371 (c)(1),
(2) Date: Jun. 3, 2019

(87) PCT Pub. No.: WO2018/104309
PCT Pub. Date: Jun. 14, 2018

(65) Prior Publication Data
US 2020/0069905 A1   Mar. 5, 2020

Related U.S. Application Data

(60) Provisional application No. 62/430,391, filed on Dec. 6, 2016.

(51) Int. Cl.
*A61M 21/00* (2006.01)
*A61B 5/00* (2006.01)
*A61B 5/375* (2021.01)

(52) U.S. Cl.
CPC ............ *A61M 21/00* (2013.01); *A61B 5/375* (2021.01); *A61B 5/4812* (2013.01);
(Continued)

(58) Field of Classification Search
CPC ............ A61M 21/00–02; A61B 5/4809–4812
See application file for complete search history.

(56) References Cited

U.S. PATENT DOCUMENTS 7,041,049 B1    5/2006  Raniere
10,232,139 B1 *  3/2019  Hang ............... A61M 21/02
(Continued)

FOREIGN PATENT DOCUMENTS

WO   2015087188 A1   6/2015
WO   2016121755 A1   8/2016

OTHER PUBLICATIONS

Ferrara, M., De Gennaro, L., Casagrande, M., & Bertini, M. (2000). Selective slow-wave sleep deprivation and time-of-night effects on cognitive performance upon awakening. Psychophysiology, 37(4), 440-446.
(Continued)

*Primary Examiner* — Thaddeus B Cox

(57) ABSTRACT

The present disclosure pertains to manipulating electrical activity in the brain of a subject to facilitate wakefulness. The system comprises: a sensory stimulator; a sensor configured to generate output signals conveying information related to brain activity, activity of the central nervous system, and/or activity of the peripheral nervous system of the subject; and a processor configured to: receive a target wake-up moment for the subject; determine one or more activity parameters of the subject during the sleep session; determine whether the one or more activity parameters indicate the subject is in deep sleep a predetermined amount of time before the target wake-up moment; and, responsive to the one or more activity parameters indicating the subject is in deep sleep, cause the one or more sensory stimulators to guide the activity parameters and facilitate/accelerate a transition from deep sleep to light sleep before the target wake-up moment.

18 Claims, 3 Drawing Sheets

(52) U.S. Cl.
CPC ............... *A61M 2021/0027* (2013.01); *A61M 2021/0044* (2013.01); *A61M 2021/0055* (2013.01); *A61M 2021/0083* (2013.01); *A61M 2205/3313* (2013.01); *A61M 2205/3344* (2013.01); *A61M 2205/50* (2013.01); *A61M 2230/06* (2013.01); *A61M 2230/10* (2013.01); *A61M 2230/14* (2013.01); *A61M 2230/42* (2013.01); *A61M 2230/50* (2013.01)

(56) References Cited

U.S. PATENT DOCUMENTS

| | | | | |
|---|---|---|---|---|
| 10,842,968 | B1* | 11/2020 | Kahn | G04B 23/02 |
| 2006/0293608 | A1* | 12/2006 | Rothman | A61B 5/369 |
| | | | | 600/545 |
| 2007/0249952 | A1* | 10/2007 | Rubin | A61B 5/4812 |
| | | | | 600/544 |
| 2011/0230790 | A1* | 9/2011 | Kozlov | A61B 5/4812 |
| | | | | 600/595 |
| 2014/0303428 | A1 | 10/2014 | Berka et al. | |
| 2015/0273177 | A1 | 10/2015 | Iizuka | |
| 2017/0312477 | A1* | 11/2017 | Hashizaki | A61M 21/02 |
| 2017/0319817 | A1 | 11/2017 | Morishima et al. | |
| 2018/0060507 | A1* | 3/2018 | Ning | G16H 50/30 |
| 2018/0078733 | A1* | 3/2018 | Freed | A61B 5/0205 |

OTHER PUBLICATIONS

Ngo, H.-V. V et al., 2012. Induction of slow oscillations by rhythmic acoustic stimulation. Journal of sleep research, p. 10 pp. Available at: http://www.ncbi.nlm.nih.gov/pubmed/22913273 [Accessed Aug. 24, 2012].

Tassi, P. & Muzet, A., 2000. Sleep inertia. Sleep medicine reviews, 4(4), pp. 341-353.

Tokley, M.J., 2009. Sleep inertia and alcohol impairment in young adults: Neurocognitive effects and interactions Implications for fire escape behaviours. Victoria University, Melbourne Australia.

International Search Report and Written Opinion, International Application No. PCT/EP2017/081536, dated Mar. 5, 2018.

* cited by examiner

SYSTEM AND METHOD FOR FACILITATING WAKEFULNESS

CROSS-REFERENCE TO PRIOR APPLICATIONS

This application is the U.S. National Phase application under 35 U.S.C. § 371 of International Application Serial No. PCT/EP2017/081536, filed on 5 Dec. 2017, which claims the benefit of U.S. Application Ser. No. 62/430,391, filed on 6 Dec. 2016. These applications are hereby incorporated by reference herein.

BACKGROUND

1. Field

The present disclosure pertains to a system and method for manipulating electrical activity in the brain of a subject to facilitate wakefulness.

2. Description of the Related Art

Systems for monitoring sleep are known. Sensory stimulation during sleep is known. Sensory stimulation during sleep is often applied continuously and/or at intervals that do not aim at influencing the sleeping patterns of a subject to cause sleep stage transitions. The present disclosure overcomes deficiencies in prior art systems.

SUMMARY

Accordingly, one or more aspects of the present disclosure relate to a system configured to facilitate wakefulness in a subject during a sleep session. The system comprises one or more sensory stimulators, one or more sensors, one or more hardware processors, and/or other components. The one or more sensory stimulators are configured to provide electric, magnetic, and/or sensory stimulation to the subject during the sleep session. The one or more sensors are configured to generate output signals conveying information related to brain activity, activity of the central nervous system, and/or activity of the peripheral nervous system of the subject. The one or more hardware processors are configured by machine readable instructions to: receive a target wake-up moment for the subject; determine one or more activity parameters of the subject during the sleep session based on the output signals; determine whether the one or more activity parameters indicate the subject is in deep sleep a predetermined amount of time before the target wake-up moment; and responsive to the one or more activity parameters indicating the subject is in deep sleep, cause the one or more sensory stimulators to control a frequency and/or an intensity of the stimulation to guide the one or more activity parameters of the subject and facilitate (e.g., accelerate and/or other facilitation) a transition from deep sleep to light sleep before the target wake-up moment such that the subject wakes from sleep naturally at or near the target wake-up moment.

Another aspect of the present disclosure relates to a method for facilitating wakefulness in a subject during a sleep session with a wakefulness system. The system comprises one or more sensory stimulators, one or more sensors, one or more hardware processors, and/or other components. The method comprises: receiving, with the one or more hardware processors, a target wake-up moment for the subject; generating, with the one or more sensors, output signals conveying information related to brain activity, activity of the central nervous system, and/or activity of the peripheral nervous system of the subject; determining, with the one or more hardware processors, one or more activity parameters of the subject during the sleep session based on the output signals; determining, with the one or more hardware processors, whether the one or more activity parameters indicate the subject is in deep sleep a predetermined amount of time before the target wake-up moment; and responsive to the one or more activity parameters indicating the subject is in deep sleep, causing, with the one or more hardware processors, the one or more sensory stimulators to control a frequency and/or an intensity of electric, magnetic, and/or sensory stimulation provided to the subject to guide the one or more activity parameters of the subject and facilitate (e.g., accelerate and/or other facilitation) a transition from deep sleep to light sleep before the target wake-up moment such that the subject wakes from sleep naturally at or near the target wake-up moment.

Yet another aspect of the present disclosure relates to a system for facilitating wakefulness in a subject during a sleep session. The system comprises: means for receiving a target wake-up moment for the subject; means for generating output signals conveying information related to brain activity, activity of the central nervous system, and/or activity of the peripheral nervous system of the subject; means for determining one or more activity parameters of the subject during the sleep session based on the output signals; means for determining whether the one or more activity parameters indicate the subject is in deep sleep a predetermined amount of time before the target wake-up moment; and means for, responsive to the one or more activity parameters indicating the subject is in deep sleep, causing means for generating electric, magnetic, and/or sensory stimulation to control a frequency and/or an intensity of electric, magnetic, and/or sensory stimulation provided to the subject to guide the one or more activity parameters of the subject and facilitate (e.g., accelerate and/or other facilitation) a transition from deep sleep to light sleep before the target wake-up moment such that the subject wakes from sleep naturally at or near the target wake-up moment.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
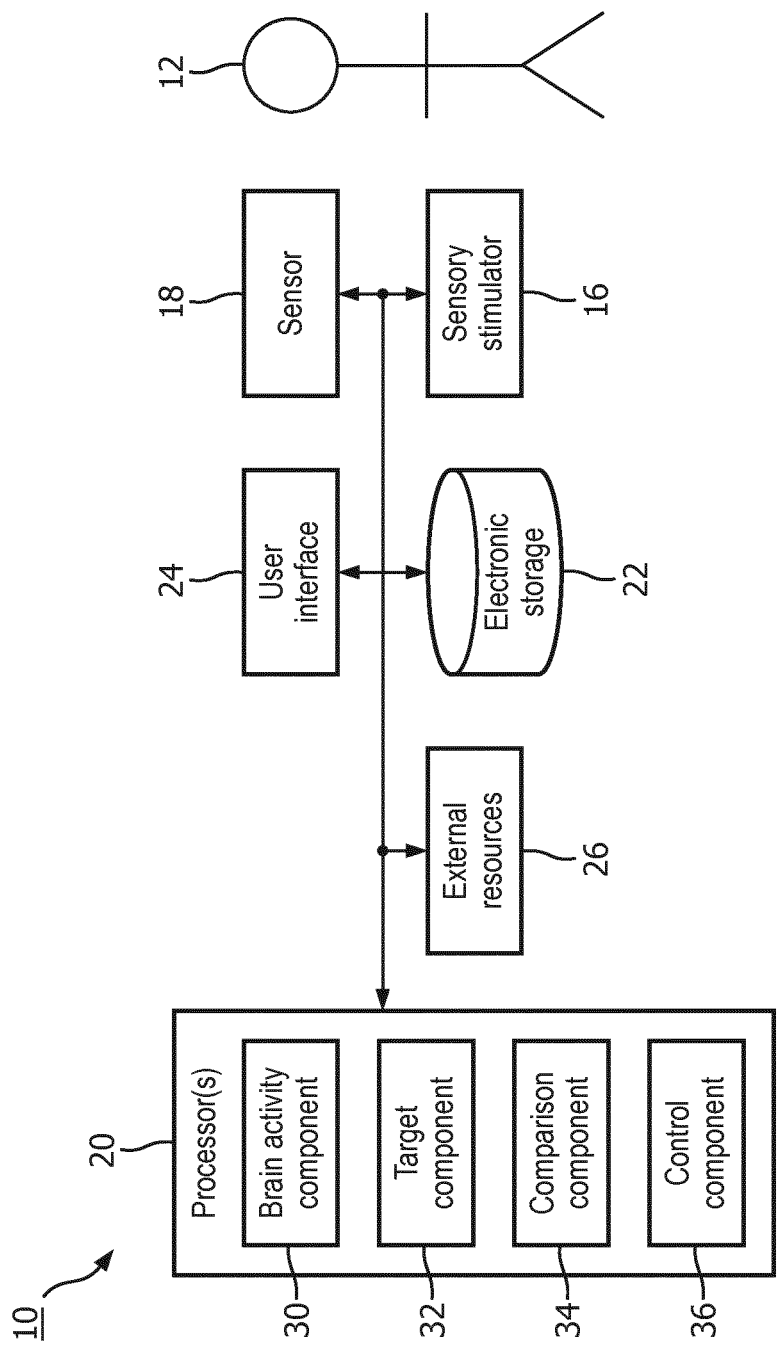
FIG. 1 is a schematic illustration of a system configured to facilitate wakefulness in a subject during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to facilitate wakefulness in a subject 12 during a sleep session. A sleep session may be and/or include a night of sleep, a nap, and/or other sleep sessions. System 10 is configured to facilitate (e.g., accelerate and/or other facilitation) transitions from deeper sleep stages to lighter sleep stages by monitoring the brain activity, activity of the central nervous system, and/or activity of the peripheral nervous system of subject 12 and providing stimulation to subject 12 to guide activity parameters. In system 10, activity information generated by sensors is used to control stimulation. Grogginess just after a wake-up alarm is common. This period of incomplete awakening, low arousal, and/or reduced ability to perform simple tasks is known as sleep inertia and is more pronounced if awakening occurs from deep sleep. Sleep inertia is characterized by a decrease in cognitive throughput that occurs after a sleep session and is exacerbated when a subject wakes from deep non-REM sleep. Impairment caused by sleep inertia is similar to the effects of alcoholic intoxication and may be dangerous for shift workers and/or others who go to work and/or engage in other activities soon after awakening.

Normal sleep is characterized by sleep stages which occur in a cyclic manner (e.g., sleep cycles) and have a different contribution to the restorative value of sleep. Typically, five sleep stages are identified with polysomnography (PSG). Stage N1 and N2 are the stages of light sleep, characterized by theta (4-8 Hz) oscillatory brain activity, and sleep spindles and K-complexes respectively. Stages N3 and N4 are the stages of deep sleep characterized with slow-waves and delta activity (0.5-4 Hz). REM sleep typically occurs after around 90 minutes of sleep onset and is characterized by increased eye movement, hearth rate, and/or respiration. These sleep stages are further described below.

To avoid sleep inertia effects, conventional systems wake a sleeping user whenever lighter sleep (e.g., stage N1 or N2) is detected. However, the lighter sleep may not occur at the alarm wake-up time set by the user. Because of this, conventional systems vary the wake-up time (e.g., either earlier or later) of the user from the desired wake-up time. This variation is often up to 30-90 minutes because the average duration of a sleep cycle in the second half of a night of sleep (and/or other sleep sessions) varies up to between 30 and 90 minutes. Such variation is not acceptable to users intending to wake up at a specific time.

Advantageously, system 10 decreases sleep inertia while still meeting a preferred wake-up time set by subject 12 and/or other users. System 10 leverages the fact that electrical brain activity (e.g., as measured by an electroencephalogram (EEG) for example) can be entrained during sleep through peripheral stimulation (e.g., auditory and/or other stimulation as described herein). System 10 modulates the brain activity of subject 12 toward faster oscillatory activity (e.g., which is characteristic of light sleep) without disturbing sleep. System 10 is configured such that the intensity, frequency, and/or other parameters of stimulation provided to subject 12 during a sleep session are modulated based on the response of subject 12 (e.g., the EEG response) to the stimulation.

For example, if subject 12 is in deep NREM (e.g., stage N3) or REM sleep about 45 minutes (for example) before the preferred wake-up time, system 10 delivers tones with a gradual decrease in the inter-tone-interval period (e.g., an increase of the EEG entrainment frequency) with sound levels just above the perception threshold (e.g. about 30 dB). This has the effect of increasing the frequency of the electrical brain activity (as measured by the EEG) which leads to lighter sleep and ultimately to wakefulness, without disturbing sleep, given the low volume of the stimulation. In some embodiments, system 10 is configured to gradually increase the volume of the stimulation with or without modifying the inter-tone-interval to gently guide the transition from deep NREM (stage N3 and/or stage N4) and/or REM sleep to wakefulness. The transition from deep sleep to light sleep comprises a transition from REM or NREM stage N3 (and/or stage N4) sleep to NREM stage N2 and/or NREM stage N1 sleep.

In some embodiments, system 10 includes one or more of a sensory stimulator 16, a sensor 18, a processor 20, electronic storage 22, a user interface 24, and/or other components.

Sensory stimulator 16 is configured to provide electric, magnetic, and/or sensory stimulation to subject 12. Sensory stimulator 16 is configured to provide electric, magnetic, and/or sensory stimulation to subject 12 prior to a sleep session, during a sleep session, and/or at other times. For example, sensory stimulator 16 may be configured to provide stimuli to subject 12 during deep (e.g., stage N3 and/or N4) sleep in a sleep session to facilitate (e.g., accelerate and/or other facilitation) a transition to a lighter stage of sleep. In some embodiments, sensory stimulator 16 may be configured such that facilitating a transition between deeper sleep stages and lighter sleep stages includes decreasing sleep slow waves in subject 12.

Sensory stimulator 16 is configured to facilitate (e.g., accelerate and/or other facilitation) transitions between sleep stages through non-invasive brain stimulation and/or other methods. Sensory stimulator 16 may be configured to facilitate transitions between sleep stages through non-invasive brain stimulation using electric, magnetic, and/or sensory stimuli. The electric, magnetic, and/or sensory stimulation may include auditory stimulation, visual stimulation, somatosensory stimulation, electrical stimulation, magnetic stimulation, a combination of different types of stimulation, and/or other stimulation. The electric, magnetic, and/or sensory stimuli include odors, sounds, visual stimulation, touches, tastes, somato-sensory stimulation, haptic, electrical, magnetic, and/or other stimuli. For example, acoustic tones may be provided to subject 12 to facilitate a transition from a deeper stage of sleep to a lighter stage of sleep. Examples of sensory stimulator 16 may include one or more of a music player, a tone generator, a collection of electrodes on the scalp of subject 12, a unit to deliver vibratory stimulation, a coil generating a magnetic field to directly stimulate the brain's cortex, light generators, a fragrance dispenser, and/or other devices. In some embodiments, sensory stimulator 16 is configured to adjust the intensity, timing, and/or other parameters of the stimulation provided to subject 12. In some embodiments, sensory stimulator 16 is configured to provide only electric and/or magnetic stimulation to subject 12.

Sensor 18 is configured to generate output signals conveying information related to brain activity, activity of the central nervous system, and/or activity of the peripheral nervous system of subject 12. The activity of subject 12 may correspond to a current sleep stage of subject 12. The current sleep stage of subject 12 may be associated with rapid eye movement (REM) sleep, non-rapid eye movement (NREM) sleep, and/or other sleep. The current sleep stage of subject 12 may be one or more of NREM stage N1, stage N2, stage N3, or stage N4 sleep, REM sleep, and/or other sleep stages. In some embodiments, NREM stage 3 and/or 4 may be slow wave (e.g., deep) sleep. Sensor 18 may comprise one or more sensors that measure such parameters directly. For example, sensor 18 may include EEG electrodes configured to detect electrical activity along the scalp of subject 12 resulting from current flows within the brain of subject 12. Sensor 18 may comprise one or more sensors that generate output signals conveying information related to activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. In some embodiments, the one or more sensors comprise one or more of the EEG electrode, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, and/or other sensors. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The one or more computer program components may comprise one or more of a brain activity component 30, a target component 32, a comparison component 34, a control component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Brain activity component 30 is configured to determine one or more activity parameters of subject 12. Brain activity component 30 is configured to determine one or more activity parameters based on the output signals from sensor 18 and/or other information. In some embodiments, determining one or more activity parameters may include generating and/or monitoring an EEG during a sleep session of subject 12. The EEG may be displayed, for example, by user interface 24. In some embodiments, brain activity component 30 is configured such that the one or more activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more activity parameters are determined based on the frequency, amplitude, and/or other characteristics of the EEG signal. In some embodiments, the determined activity parameters and/or the characteristics of the EEG may be and/or indicate sleep stages that correspond to the REM and/or NREM sleep stages described above. In some embodiments, the determined activity parameters are the REM and/or NREM sleep stages described above.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 2 Hz), also known as sleep slow waves, with peak-to-peak amplitudes greater than about 75 uV for sleep stage N3 and/or N4; and/or other characteristics. In some embodiments, light sleep may be characterized by the fact that the alpha activity (e.g., EEG power in the 8-12 Hz band) is no longer present and slow wave activity is not present. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, brain activity component 30 is configured to determine the one or more activity parameters at predetermined times (e.g., intervals), substantially continuously, and/or at other times. In some embodiments, activity parameters may be determined based on electrocardiogram (ECG) signals, actigraphy signals, body temperature signals, galvanic skin response (GSR) signals, and/or other information related to the central and/or peripheral nervous systems of subject 12. In some embodiments, in addition to and/or instead of distinguishing between the different sleep stages described above, brain activity component 30 is configured to distinguish between light sleep and deep sleep (e.g., as described above) in a binary manner.

Target component 32 is configured to receive a target wake-up moment for subject 12. In some embodiments, the target wake-up moment may be a time of day, an amount of time in the future, and/or other moments. The target wake-up moment may be a moment when subject 12 and/or other users desire to wake from sleep (e.g., from a night of sleep, a nap, etc.). For example, subject 12 and/or other users may set (e.g., via user interface 24) his own wake-up time prior to going to sleep. In some embodiments, target component 32 is configured such that subject 12 and/or other users may enter and/or select information related to the target wake-up moment via a user interface (e.g., user interface 24 described herein) and/or other components of system 10. For example, target component 32 may control user interface 24 to display one or more fields in one or more views of a graphical user interface that facilitate entry and/or selection of a wake-up time. In some embodiments, the target wake-up moment may be received in other ways. For example, in some embodiments, receiving a target wake-up moment may include determining the wake-up moment based on previous sleep sessions of subject 12, determining the wake-up moment based on previous sleep sessions of a population of subjects that are related to subject 12, receiving the information from external computing systems (e.g., an alarm clock wake-up system), obtaining information determined at manufacture, and/or obtaining the information by other methods.

Comparison component 34 is configured to determine whether the one or more activity parameters indicate subject 12 is in deep sleep a predetermined amount of time before the target wake-up moment. In some embodiments, the predetermined amount of time may be obtained from and/or determined based on external normative data that specifies (using, for example, demographically matched information) the recommended duration of deep sleep for subject 12. Such normative data can be obtained from, for example, papers similar to and/or the same as "Ohayon, M. M., Carskadon, M. a, Guilleminault, C., & Vitiello, M. V. (2004). Meta-analysis of quantitative sleep parameters from childhood to old age in healthy individuals: developing normative sleep values across the human lifespan. Sleep, 27(7), 1255-1273" and/or other sources of data. By way of non-limiting examples, the predetermined amount of time may be determined based on recommended amounts of time in deep sleep including: for age range 20-30 years, about 17.5±4.5 percent of total sleep in a sleep session (e.g., 74.9±19.7 minutes of a typical nocturnal sleep session); for age range 30-40 years, about 13.2±7.4 percent of total sleep in a sleep session (e.g., 54.3±30.5 minutes of a typical nocturnal sleep session); and for age range 40-50 years, about 13.7±7.4 percent of total sleep in a sleep session (e.g., 54.3±29.3 minutes of a typical nocturnal sleep session).

In some embodiments, comparison component 34 is configured to determine whether the one or more activity parameters indicate subject 12 is in deep sleep a predetermined amount of time before the target wake-up moment by comparing the one or more activity parameters to target ranges for the one or more activity parameters that correspond to deep sleep and/or light sleep. For example, in embodiments where the one or more activity parameters include and/or are the sleep stages themselves, comparison component 34 is configured to compare a current sleep stage (e.g., N3) of subject 12 at the predetermined amount of time before the target wake-up moment to target sleep stages (e.g., N2 and/or N1) for that time. As another example, in some embodiments, determining whether the one or more activity parameters indicate the subject is in deep sleep a predetermined amount of time before the target wake-up moment includes comparing the one or more activity parameters to target ranges. In some embodiments, comparing the one or more activity parameters to target ranges includes comparing a given activity parameter (e.g., a density of slow waves, an EEG band power ratio, etc.) to one or more threshold values for that parameter that indicate lighter sleep. Comparison component 34 may determine whether the given activity parameter is in a target range based on whether the given activity parameter has breached one or more of the threshold values. For example, brain activity component 30 may determine that subject 12 is in stage N3 sleep based on a ratio of the power levels in the beta band and the delta band of the EEG and pre-programmed power level ratio thresholds (e.g., determined at manufacture) for individual sleep stages. Comparison component 34 may be configured to compare the current power level ratio determined by brain activity component 30 to previously determined threshold ratios for stage N2 and/or N1 sleep to determine that subject 12 is not in stage N2 or N1 sleep.

Control component 36 is configured to control sensory stimulator 16 to provide stimulation to subject 12 to guide the activity parameters of subject 12. Control component 36 is configured to, responsive to comparison component 34 (e.g., via the one or more activity parameters) indicating subject 12 is in deep sleep at the given amount of time before the target wake-up moment, cause sensory stimulator 16 to control a frequency and/or an intensity of the stimulation to guide the one or more activity parameters of subject 12. The one or more activity parameters are guided to facilitate (e.g., accelerate and/or other facilitation) a transition from deep sleep to light sleep before the target wake-up moment. The one or more activity parameters are guided to facilitate a transition from deep sleep to light sleep before the target wake-up moment such that subject 12 wakes from sleep naturally at or near the target wake-up moment. In some embodiments, the one or more activity parameters are related to slow wave activity (SWA) of the subject, and controlling the frequency and/or intensity of the stimulation influences SWA in the subject to facilitate a gradual transition from deep sleep to light sleep. In some embodiments, the one or more hardware processors are configured such that the one or more activity parameters are related to EEG power in a predetermined frequency (e.g., power in the delta (from 0.5 to 4 Hz) frequency band, power in the theta (from 4 to 8 Hz) frequency band, power in the alpha (from 8 to 12 Hz) frequency band, and/or power in the beta (from 15 to 30 Hz) frequency band) band for the subject, and controlling the frequency and/or intensity of the stimulation influences the EEG power in the predetermined frequency band for the subject to facilitate a gradual transition from deep sleep to light sleep. In some embodiments, the transition from deep sleep to light sleep comprises a transition from REM or NREM stage N3 and/or N4 sleep to NREM stage N2 and/or NREM stage N1 sleep, and/or other sleep stages. In some embodiments, control component 36 is configured to control sensory stimulator 16 to provide stimulation to subject 12 to guide the activity parameters (e.g., sleep stage, density of slow waves, EEG power band ratios, etc.) of subject 12 into ranges that indicate light sleep responsive to the activity parameters of subject 12 being outside ranges that indicate light sleep for those parameters.

Controlling sensory stimulator 16 includes determining a timing, a frequency, an intensity, and/or other parameters of the stimulation provided to subject 12. The timing, frequency, intensity, and/or other parameters of the stimulation provided to subject 12 may be controlled to decrease sleep slow waves, for example, in subject 12 during the sleep session to facilitate (e.g., accelerate and/or other facilitation) transition from deeper sleep stages to lighter sleep stages. The timing, frequency, intensity, and/or other parameter determinations are based on previous sleep sessions of subject 12, sleep sessions of a representative group of subjects related to subject 12, may be determined at manufacture, determined based on the output signals from sensors 18, and/or determined by other methods.

In some embodiments, control component 36 is configured to control sensory stimulator 16 such that the timing of the sensory stimuli (e.g., auditory tones) comprises a regular, repeating interval of time between individual stimuli delivered to subject 12. This type of stimulation may influence the EEG by entraining the electrical activity of the brain of subject 12. The possibility of inducing electrical activity at higher, lower, and/or other timings, frequencies, and/or intensities of stimulation to facilitate (e.g., accelerate and/or other facilitation) transitions from N4 and/or N3 to N2, from N2 to N1, and/or between any other sleep stages is also contemplated. For example, in some embodiments, control component 36 is configured such that the timing of the stimulation is variable between individual stimuli. In some embodiments, the stimulation is tailored by control component 36 based on the information from sensor 18, brain activity component 30, target component 32, comparison component 34, and/or other sources. The stimulation is tailored by control component 36 to entrain the EEG in the frequency band(s) where discrepancies (e.g., including both deficits and/or excess) exist between the activity parameter range for a target sleep stage (e.g., stage N2 and/or stage N1) and the activity parameters for the current sleep stage (e.g., stage N4, stage N3 and/or REM).

In some embodiments, control component 36 may control sensory stimulator 16 to provide the stimulation during the sleep session such that the stimulation does not unintentionally wake subject 12. Controlling sensory stimulator 16 to provide stimulation so subject 12 is not unintentionally aroused from sleep may be accomplished by controlling the timing, frequency, intensity, and/or other parameters of the stimulation.

For example, control component 36 may control sensory stimulator 16 to provide the stimulation at a low intensity level when subject 12 is to transition to a lighter sleep stage but remain asleep and at a high intensity level if subject 12 is to be aroused from sleep (described below). Control component 36 may be configured such that the intensity of the stimulation is adjusted based on the likelihood of producing arousals. Control component 36 is configured to determine the likelihood of producing arousals based on the instantaneous EEG power in the beta band, and/or by other methods. In some embodiments, comparison component 34 may determine whether subject 12 is awake at the target wake-up moment. Responsive to subject 12 remaining in light sleep at the target wake-up moment, control component 36 is configured to cause one or more sensory stimulators 16 to control the frequency and/or the intensity of the stimulation to wake subject 12.

Figure 2:
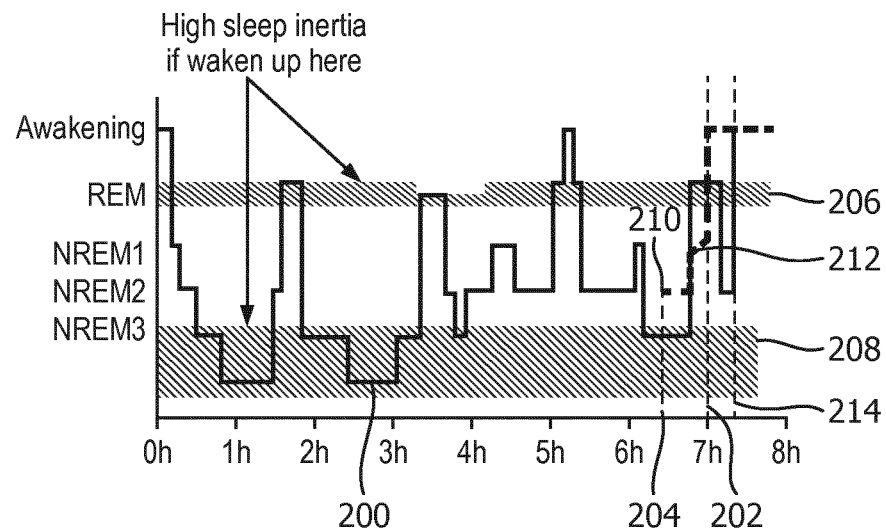
FIG. 2 graphically illustrates operations performed by system.

FIG. 2 graphically illustrates operations performed by system 10 (shown in FIG. 1). In FIG. 2, line 200 depicts the sleep architecture of subject 12 during a sleep session. In this example, system 10 has received a target wake-up moment 202 (e.g., 7 AM) from subject 12 (FIG. 1). A predetermined amount of time 204 (e.g. 45 mins) before target wake-up moment 202, system 10 determines whether subject 12 is in deep sleep 206, 208 (e.g., REM and/or stage N4/N3 as described above). In this example, subject 12 is in stage N3 sleep 208. Responsive to a determination that subject 12 is in deep sleep (e.g., sleep 208) at the predetermined time 204, system 10 begins stimulating (e.g., via auditory tones) 210 subject 12. As shown in FIG. 2, dotted line 212 indicates that subject 12 is gradually guided out of deep sleep into stage N2 and then stage N1 sleep, which facilitates waking up without feeling groggy. Guiding subject 12 into stage N2 and then N1 sleep before target wake-up moment 202 increases the probability that subject 12 wakes up naturally close to (but not later than) target wake-up moment 202. In this example, had subject 12 used a conventional alarm system, the conventional system would have delayed 214 the wake up time by 18 minutes to wait for line 200 to indicate that subject 12 was no longer in stage N3 sleep 208 or REM sleep 206.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to (e.g., a target wake-up moment) and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 includes sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. For example, in some embodiments, external resources 26 include one or more external lighting devices controlled by processor 20 to provide stimulation to subject 12. In some implementations, some or all of the functionality attributed herein to external resources 26 may be provided by resources included in system 10. External resources 26 may be configured to communicate with processor 20, user interface 24, sensor 18, electronic storage 22, and/or other components of system 10 via wired and/or wireless connections, via a network (e.g., a local area network and/or the internet), via cellular technology, via Wi-Fi technology, and/or via other resources.

Figure 3:
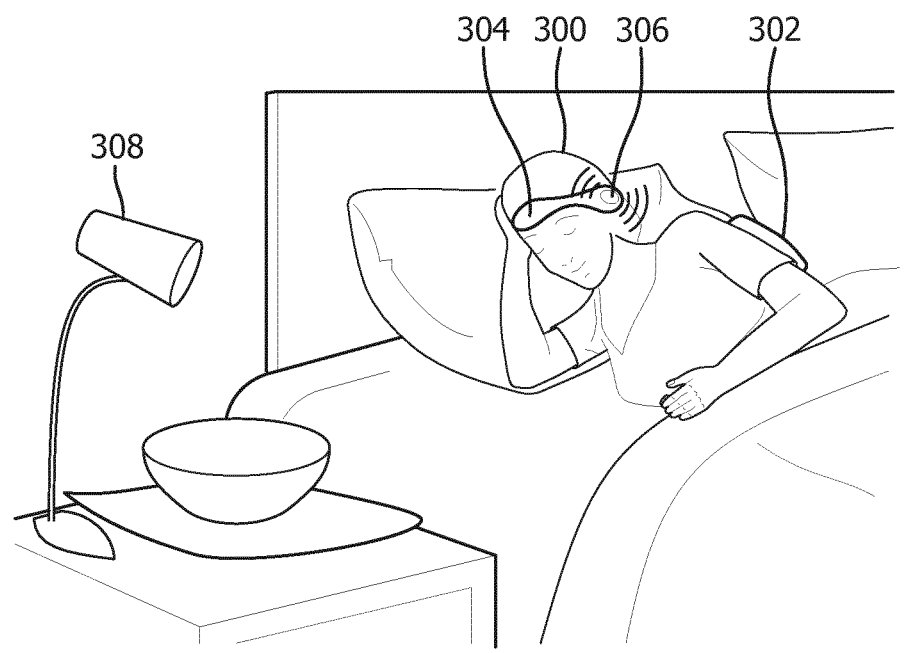
FIG. 3 illustrates a headset worn by a subject that includes sensing electrodes and a wireless audio device.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 3 illustrates a headset 300 worn by a subject 302 that includes sensing electrodes 304, and a wireless audio device 306. Sensing electrodes 304 may be represented, for example, by sensor 18 in FIG. 1. Wireless audio device 306 may be represented, for example, by sensory stimulator 16 shown in FIG. 1. FIG. 3 also illustrates a lamp 308 (e.g., part of external resources 26) controlled by system 10 to generate light with a given intensity and/or frequency to facilitate wakefulness in subject 302.

Figure 4:
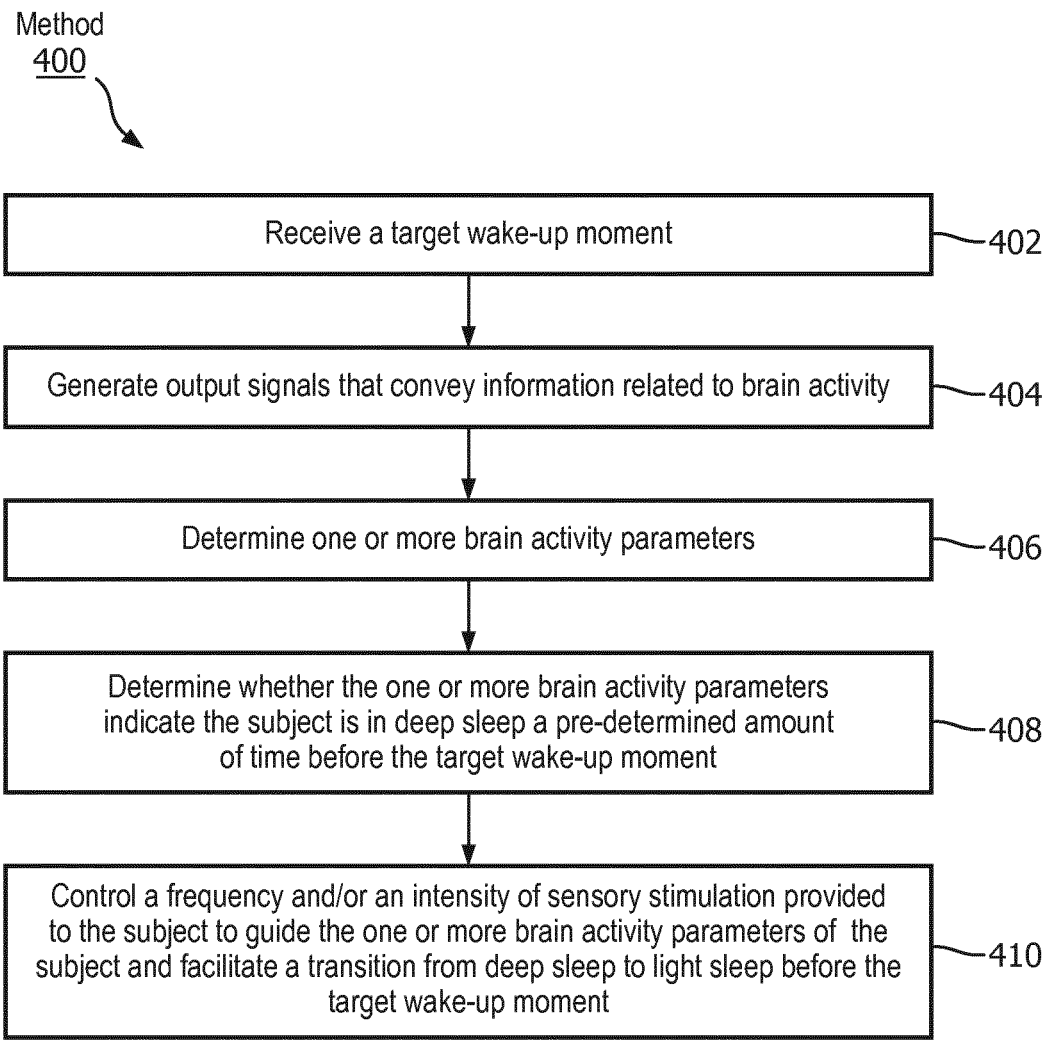
FIG. 4 illustrates a method for facilitating wakefulness in a subject with a wakefulness system.

FIG. 4 illustrates a method 400 for facilitating wakefulness a subject with a wakefulness system. The system comprises one or more sensory stimulators, one or more sensors, one or more hardware processors, and/or other components. The one or more hardware processors are configured to execute computer program components. The computer program components comprise a brain activity component, a target component, a comparison component, a control component, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a target wake-up moment may be received. In some embodiments, the target wake-up moment may be a time of day, an amount of time in the future, and/or other moments. The target wake-up moment may be a moment when the subject and/or other users wish to wake from sleep. In some embodiments, the subject and/or other users may enter and/or select the target wake-up moment via a user interface (e.g., user interface 24 described above) and/or other components of the system. In some embodiments, the target wake-up moment may be received in other ways. In some embodiments, operation 402 is performed by a processor component the same as or similar to target component 32 (shown in FIG. 1 and described herein).

At an operation 404, output signals conveying information related to brain activity, activity of the central nervous system, and/or activity of the peripheral nervous system are generated. In some embodiments, the one or more sensors comprise one or more of an EEG electrode, an EOG electrode, an actigraphy sensor, an EKG electrode, a respiration sensor, a pressure sensor, a vital signs camera, a PPG sensor, an fNIR sensor, and/or other sensors. In some embodiments, the system may be configured to generate an EEG based on the output signals. In some embodiments, operation 404 is performed by one or more sensors the same as or similar to sensors 18 (shown in FIG. 1 and described herein).

At an operation 406, one or more activity parameters are determined. The one or more activity parameters may be determined based on the output signals and/or other information. In some embodiments, the activity parameters may be determined based on the EEG, for example. The one or more activity parameters may be related to a frequency of the EEG and/or other parameters. In some embodiments, operation 406 may include determining a current sleep stage of the subject. In some embodiments, operation 406 is performed by a processor component the same as or similar to brain activity component 30 (shown in FIG. 1 and described herein).

Operation 408 includes determining whether the one or more activity parameters indicate the subject is in deep sleep (e.g., stage N3) a predetermined amount of time before the target wake-up moment. In some embodiments, the current sleep stage may be compared to target sleep stages (e.g., N1 and/or N2) corresponding to that moment of the sleep session. In some embodiments, operation 408 is performed by a processor component the same as or similar to comparison component 34 (shown in FIG. 1 and described herein).

At an operation 410, the sensory stimulators are controlled to provide electric, magnetic, and/or sensory stimulation to the subject. In some embodiments, the stimulation comprises one or more of auditory stimulation, visual stimulation, somatosensory stimulation and/or other stimulation. The sensory stimulators are controlled to provide stimulation to the subject to guide the activity parameters of the subject. The sensory stimulators are controlled such that a frequency and/or an intensity of stimulation provided to the subject guides the one or more activity parameters of the subject and facilitates (e.g., accelerates and/or other facilitation) a transition from deep sleep to light sleep before the target wake-up moment. In some embodiments, responsive to the one or more activity parameters indicating the subject is in deep sleep, the sensory stimulators are controlled to provide stimulation to the subject to cause the current sleep stage of the subject to transition to a lighter sleep stage. In some embodiments, the one or more sensory stimulators control the frequency and/or intensity of stimulation provided to the subject to guide the one or more activity parameters of the subject and facilitate a transition from deep sleep to light sleep before the target wake-up moment such that the subject wakes from sleep naturally at or near the target wake-up moment. In some embodiments, responsive to the subject already being in a lighter sleep stage (e.g., N1, N2), the system is configured to facilitate natural waking with little to no stimulation provided to the subject.

In some embodiments, the one or more activity parameters are related to SWA in the subject, and controlling the frequency and/or intensity of the stimulation influences SWA in the subject to facilitate a gradual transition from deep sleep to light sleep. In some embodiments, the one or more hardware processors are configured such that the one or more activity parameters are related to EEG power in a predetermined frequency (e.g., power in the delta (from 0.5 to 4 Hz) frequency band, power in the theta (from 4 to 8 Hz) frequency band, power in the alpha (from 8 to 12 Hz) frequency band, and/or power in the beta (from 15 to 30 Hz) frequency band) band for the subject, and controlling the frequency and/or intensity of the stimulation influences the EEG power in the predetermined frequency band for the subject to facilitate a gradual transition from deep sleep to light sleep. In some embodiments, the transition from deep sleep to light sleep comprises a transition from REM or NREM Stage 3 sleep to NREM Stage 2 and/or NREM Stage 1 sleep. In some embodiments, operation 410 includes determining whether the subject is awake at the target wake-up moment. Responsive to the subject remaining in light sleep (e.g., after being led from deep sleep to light sleep by the system) at the target wake-up moment, operation 410 may include causing the one or more sensory stimulators to control the frequency and/or the intensity of the stimulation to wake the subject. In some embodiments, operation 410 is performed by a processor component the same as or similar to control component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to facilitate wakefulness in a subject during a sleep session, the system comprising:
   one or more sensory stimulators configured to provide electric, magnetic, and/or sensory stimulation to the subject during the sleep session;
   one or more sensors configured to generate output signals conveying information related to brain activity, activity of the central nervous system, and/or activity of the peripheral nervous system of the subject; and
   one or more hardware processors configured by machine readable instructions to:
     receive a target wake-up moment for the subject;
     determine one or more activity parameters of the subject during the sleep session based on the output signals;
     determine whether the one or more activity parameters indicate the subject is in deep sleep a predetermined amount of time before the target wake-up moment, wherein the predetermined amount of time before the target wake-up moment is determined based on external data that specifies a recommended duration of deep sleep for subjects demographically similar to the subject; and
     responsive to the one or more activity parameters indicating the subject is in deep sleep at the predetermined amount of time before the target wake-up moment, cause the one or more sensory stimulators to control a frequency and/or an intensity of the stimulation to guide the one or more activity parameters of the subject and facilitate a transition from deep sleep to light sleep before the target wake-up moment such that the subject wakes from sleep naturally at or near, and no later than, the target wake-up moment, wherein the target wake-up moment comprises either a time of day or a duration of time that constitutes an amount of time in the future.

2. The system of claim 1, wherein the one or more hardware processors are configured such that the one or more activity parameters are related to electroencephalogram (EEG) power in a predetermined frequency band for the subject, and wherein controlling the frequency and/or intensity of the stimulation influences the EEG power in the predetermined frequency band for the subject to facilitate a gradual transition from deep sleep to light sleep.

3. The system of claim 1, wherein the one or more hardware processors are configured such that the transition from deep sleep to light sleep comprises a transition from REM or NREM Stage 3 sleep to NREM Stage 2 and/or NREM Stage 1 sleep.

4. The system of claim 1, wherein the one or more hardware processors are further configured to determine whether the subject is awake at the target wake-up moment, and, responsive to the subject remaining in light sleep at the target wake-up moment, cause the one or more sensory stimulators to control the frequency and/or the intensity of the electric, magnetic, and/or sensory stimulation to wake the subject.

5. The system of claim 1, wherein the one or more sensory stimulators are configured such that the electric, magnetic, and/or sensory stimulation comprises one or more of auditory stimulation, visual stimulation, electrical stimulation, magnetic stimulation, or somatosensory stimulation.

6. The system of claim 1, wherein the one or more sensors comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, a temperature sensor, or a functional near infra-red (fNIR) sensor.

7. A method for facilitating wakefulness in a subject during a sleep session with a wakefulness system, the system comprising one or more sensory stimulators, one or more sensors, and one or more hardware processors, the method comprising:
   receiving, with the one or more hardware processors, a target wake-up moment for the subject;
   generating, with the one or more sensors, output signals conveying information related to brain activity, activity of the central nervous system, and/or activity of the peripheral nervous system of the subject;
   determining, with the one or more hardware processors, one or more activity parameters of the subject during the sleep session based on the output signals;
   determining, with the one or more hardware processors, whether the one or more activity parameters indicate the subject is in deep sleep a predetermined amount of time before the target wake-up moment, wherein the predetermined amount of time before the target wake-up moment is determined based on external data that specifies a recommended duration of deep sleep for subjects demographically similar to the subject; and
   responsive to the one or more activity parameters indicating the subject is in deep sleep at the predetermined amount of time before the target wake-up moment, causing, with the one or more hardware processors, the one or more sensory stimulators to control a frequency and/or an intensity of electric, magnetic, and/or sensory stimulation provided to the subject to guide the one or more activity parameters of the subject and facilitate a transition from deep sleep to light sleep before the target wake-up moment such that the subject wakes from sleep naturally at or near, and no later than, the target wake-up moment,
   wherein the target wake-up moment comprises either a time of day or a duration of time that constitutes an amount of time in the future.

8. The method of claim 7, wherein the one or more activity parameters are related to electroencephalogram (EEG) power in a predetermined frequency band for the subject, and wherein controlling the frequency and/or intensity of the stimulation influences the EEG power in the predetermined band for the subject to facilitate a gradual transition from deep sleep to light sleep.

9. The method of claim 7, wherein the transition from deep sleep to light sleep comprises a transition from REM or NREM Stage 3 sleep to NREM Stage 2 and/or NREM Stage 1 sleep.

10. The method of claim 7, further comprising determining, with the one or more hardware processors, whether the subject is awake at the target wake-up moment, and, responsive to the subject remaining in light sleep at the target wake-up moment, causing, with the one or more hardware processors, the one or more sensory stimulators to control the frequency and/or the intensity of the stimulation to wake the subject.

11. The method of claim 7, wherein the electric, magnetic, and/or sensory stimulation comprises one or more of auditory stimulation, visual stimulation, electrical stimulation, magnetic stimulation, or somatosensory stimulation.

12. The method of claim 7, wherein the one or more sensors comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, a temperature sensor, or a functional near infra-red (fNIR) sensor.

13. A system for facilitating wakefulness in a subject during a sleep session, the system comprising:
   means for receiving a target wake-up moment for the subject;
   means for generating output signals conveying information related to brain activity, activity of the central nervous system, and/or activity of the peripheral nervous system of the subject;
   means for determining one or more activity parameters of the subject during the sleep session based on the output signals;
   means for determining whether the one or more activity parameters indicate the subject is in deep sleep a predetermined amount of time before the target wake-up moment, wherein the predetermined amount of time before the target wake-up moment is determined based on external data that specifies a recommended duration of deep sleep for subjects demographically similar to the subject; and
   means for, responsive to the one or more activity parameters indicating the subject is in deep sleep at the predetermined amount of time before the target wake-up moment, causing means for generating electric, magnetic, and/or sensory stimulation to control a frequency and/or an intensity of electric, magnetic, and/or sensory stimulation provided to the subject to guide the one or more activity parameters of the subject and facilitate a transition from deep sleep to light sleep before the target wake-up moment such that the subject wakes from sleep naturally at or near, and no later than, the target wake-up moment, wherein the target wake-up moment comprises either a time of day or a duration of time that constitutes an amount of time in the future.

14. The system of claim 13, wherein the one or more activity parameters are related to electroencephalogram (EEG) power in a predetermined frequency band for the subject, and wherein controlling the frequency and/or intensity of the stimulation influences the EEG power in the predetermined band for the subject to facilitate a gradual transition from deep sleep to light sleep.

15. The system of claim 13, wherein the transition from deep sleep to light sleep comprises a transition from REM or NREM Stage 3 sleep to NREM Stage 2 and/or NREM Stage 1 sleep.

16. The system of claim 13, further comprising means (20) for determining whether the subject is awake at the target wake-up moment, and, means (20) for, responsive to the subject remaining in light sleep at the target wake-up moment, causing the means for generating electric, magnetic, and/or sensory stimulation to control the frequency and/or the intensity of the stimulation to wake the subject.

17. The system of claim 13, wherein the electric, magnetic, and/or sensory stimulation comprises one or more of auditory stimulation, visual stimulation, electrical stimulation, magnetic stimulation, or somatosensory stimulation.

18. The system of claim 13, wherein the means for generating output signals comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, a temperature sensor, or a functional near infra-red (fNIR) sensor.

* * * * *